(12) United States Patent
Flagler (10) Patent No.: US 8,251,739 B2
(45) Date of Patent: *Aug. 28, 2012

(54) METHOD AND APPARATUS FOR ALIGNING AND SECURING A CABLE STRAIN RELIEF

(75) Inventor: Robert W. Flagler, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/290,922

(22) Filed: Nov. 7, 2011

(65) Prior Publication Data

US 2012/0053430 A1 Mar. 1, 2012

Related U.S. Application Data

(63) Continuation of application No. 12/343,791, filed on Dec. 24, 2008, now Pat. No. 8,070,508.

(60) Provisional application No. 61/009,718, filed on Dec. 31, 2007.

(51) Int. Cl.
*H01R 13/58* (2006.01)

(52) U.S. Cl. ....................................... 439/470; 439/455

(58) Field of Classification Search .................. 439/470, 439/449, 452, 455, 464, 465; 600/344
See application file for complete search history.

(56) References Cited

U.S. PATENT DOCUMENTS

| | | | | |
|---|---|---|---|---|
| 6,112,107 A * | 8/2000 | Hannula | ...................... | 600/310 |
| 6,428,344 B1 * | 8/2002 | Reed | ............................. | 439/455 |
| 7,008,257 B2 * | 3/2006 | Zhu et al. | ..................... | 439/470 |
| 8,070,508 B2 * | 12/2011 | Flagler | ......................... | 439/470 |

* cited by examiner

*Primary Examiner* — Hae Moon Hyeon
(74) *Attorney, Agent, or Firm* — Fletcher Yoder (57) ABSTRACT

The present disclosure relates to a strain relief. In various embodiments, the strain relief includes a strain relief body and at least one alignment feature. The strain relief body is configured to provide support for connection of a cable and/or a wire lead of the cable to a frame. The alignment feature is configured to facilitate alignment of the strain relief relative to the frame. In various embodiments, provided are methods of manufacturing a sensor with a strain relief. The methods may include forming the strain relief about a cable and/or wire leads, wherein the strain relief comprises at least one alignment feature, aligning the alignment feature of the strain relief to a complementary alignment feature of a frame, engaging the complementary alignment feature of the frame with the alignment feature of the strain relief, and electrically coupling the cable and/or wire leads to a circuit.

20 Claims, 10 Drawing Sheets

METHOD AND APPARATUS FOR ALIGNING AND SECURING A CABLE STRAIN RELIEF

CROSS-REFERENCE TO RELATED APPLICATIONS

This application is a continuation of U.S. patent application Ser. No. 12/343,791, entitled "Method and Apparatus for Aligning and Securing a Cable Strain Relief", filed Dec. 24, 2008, which in turn claims priority to U.S. Provisional Application No. 61/009,718, filed Dec. 31, 2007, both of which are incorporated herein by reference in their entirety for all purposes.

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One such monitoring technique is commonly referred to as pulse oximetry. Pulse oximetry may be used to measure various blood flow characteristics, such as the blood-oxygen saturation of hemoglobin in arterial blood and/or the rate of blood pulsations corresponding to each heartbeat of a patient.

The devices based upon pulse oximetry techniques are commonly referred to as pulse oximeters. Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

Pulse oximetry sensors may include a flex circuit that electrically connects various electrical components of the sensor. For example, components of the flex circuit may include an optical emitter, such as an LED, a photodetector and wires forming conductors which electrically connect the sensor components and/or allow connection of the sensor components to a pulse oximeter monitor via wire leads contained in a cable. During use of such a sensor, mechanical stresses may be placed on the location where an external cable and its wire leads are attached to the sensor frame and associated flex circuit. Generally, a strain relief may be provided to reduce the effect of the mechanical stresses at the point where the cable attaches to the sensor frame.

During the manufacturing process it may be labor intensive to secure a strain relief to the sensor frame and cable prior to and during the process of connecting the wire leads of the cable to the flex circuit. Further, aligning the wire leads for proper connection may be a labor intensive task, the difficulty of which may result in wires being improperly seated, resulting in the production of poorly functioning or non-functioning sensors.

SUMMARY

Certain aspects commensurate in scope with the disclosure are set forth below. It should be understood that these aspects are presented merely to provide the reader with a brief summary of certain forms the disclosure might take and that these aspects are not intended to limit the scope of the disclosure. Indeed, the disclosure may encompass a variety of aspects that may not be set forth below.

In accordance with various embodiments, a strain relief is provided. The strain relief includes a strain relief body and at least one alignment feature. The strain relief body is configured to provide support for connection of a cable and/or at least one wire lead of the cable to a frame. The at least one alignment feature is configured to facilitate alignment of the strain relief relative to the frame.

In accordance with various embodiments, provided is a method of manufacturing a sensor with a strain relief. The method includes forming the strain relief about a cable and/or wire leads, wherein the strain relief comprises at least one alignment feature. The alignment feature of the strain relief is aligned to a complementary alignment feature of a frame. The complementary alignment feature of the frame is engaged with the alignment feature of the strain relief. The cable and/or wire leads are electrically coupled to a circuit.

In accordance with various embodiments, provided is a sensor system. The sensor system includes a frame, a cable, and a strain relief. The strain relief includes a first strain relief portion couplable to the frame and coupled to the cable and a second strain relief portion coupable to the first strain relief portion and a portion of the cable, proximate to a location where the cable exits the sensor.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Various embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

According to various embodiments, methods and systems for securing a cable and strain relief to a sensor frame during the fabrication of a sensor are described. In one embodiment, the cable and wire leads of the cable are secured to the sensor frame via a strain relief that is aligned and secured to the frame. In such an embodiment, the cable and strain relief may be secured to the sensor frame by sliding the strain relief into the frame. In another embodiment, the strain relief provides for aligning the wire leads of the cable for connection to a flex circuit. In such an embodiment, the strain relief and cable may be secured to the frame with the wire leads in position for soldering, and with minimal, or at least a reduced amount, of additional alignment of the wire leads.

As described herein, various embodiments of the sensor and frame are provided which are believed to provide simple and secure assembly of a sensor including a frame and a strain relief. Prior to discussing such sensors in detail, it should be appreciated that such sensors are typically designed for use with a patient monitoring system. For example, referring now to FIG. 1, a sensor 10 according to an embodiment may be used in conjunction with a patient monitor 12. In the depicted embodiment, a cable 14 connects the sensor 10 to the patient monitor 12. As will be appreciated by those of ordinary skill in the art, the sensor 10 and/or the cable 14 may include or incorporate one or more integrated circuit devices or electrical devices, such as a memory, processor chip, or resistor, that may facilitate or enhance communication between the sensor 10 and the patient monitor 12. Likewise the cable 14 may be an adaptor cable, with or without an integrated circuit or electrical device, for facilitating communication between the sensor 10 and various types of monitors, including older or newer versions of the patient monitor 12 or other physiological monitors.

Figure 1:
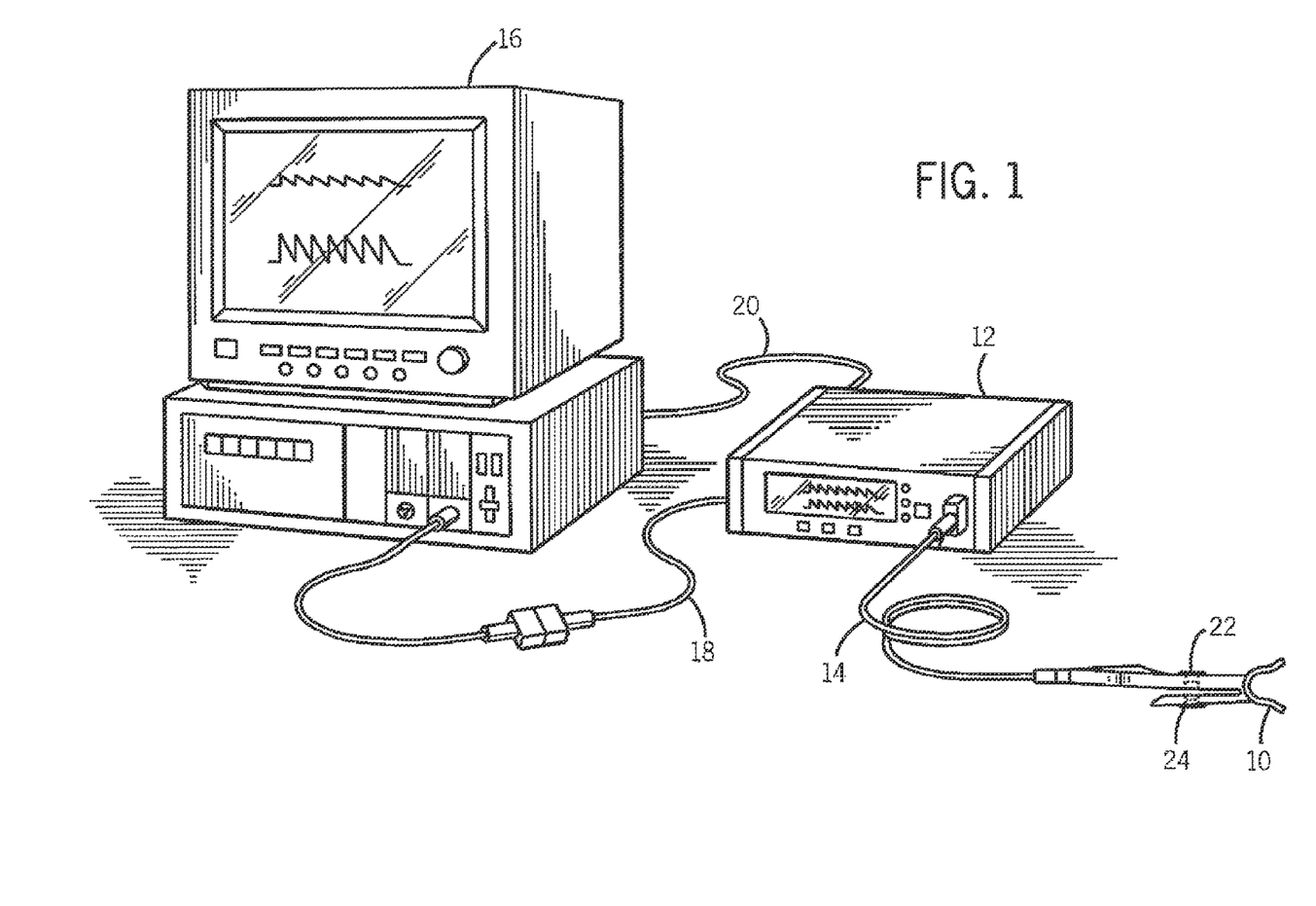
FIG. 1 illustrates a patient monitoring system coupled to a multi-parameter patient monitor and a sensor, in accordance with an embodiment.

In other embodiments, the sensor 10 and the patient monitor 12 may communicate via wireless means, such as using radio, infrared, or optical signals. In such embodiments, a transmission device (not shown) may be connected to the sensor 10 to facilitate wireless transmission between the sensor 10 and the patient monitor 12. As will be appreciated by those of ordinary skill in the art, the cable 14 (or a corresponding wireless transmission) may be used to transmit control or timing signals from the monitor 12 to the sensor 10 and/or to transmit acquired data from the sensor 10 to the monitor 12. In some embodiments, the cable 14 may be an optical fiber that enables optical signals to be conducted between the patient monitor 12 and the sensor 10.

In an embodiment, the patient monitor 12 may be a suitable pulse oximeter, such as those available from Nellcor Puritan Bennett LLC. In other embodiments, the patient monitor 12 may be a monitor suitable for measuring tissue water fractions, or other body fluid related metrics, using spectrophotometric or other techniques. Furthermore, the patient monitor 12 may be a multi-purpose monitor suitable for performing pulse oximetry and measurement of tissue water fraction, or other combinations of physiological and/or biochemical monitoring processes, using data acquired via the sensor 10. Furthermore, to upgrade conventional monitoring functions provided by the monitor 12 and to provide additional functions, the patient monitor 12 may be coupled to a multi-parameter patient monitor 16 via a cable 18 connected to a sensor input port and/or a cable 20 connected to a digital communication port.

In an embodiment, the sensor 10, as depicted in FIG. 1, is a clip-style sensor that is overmolded to provide a unitary or enclosed assembly. The sensor 10 may include an emitter 22 and a detector 24 which may be of any suitable type. For example, the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the sensor 10 is coupled to a cable 14 that is responsible for transmitting electrical and/or optical signals to and from the emitter 22 and the detector 24 of the sensor 10. The cable 14 may be permanently coupled to the sensor 10, or it may be removably coupled to the sensor 10—the latter alternative being more useful and cost efficient in situations where the sensor 10 is disposable.

The sensor 10 discussed herein may be configured for either transmission or reflectance type sensing, in various embodiments. Furthermore, the sensor 10 may include various structural and functional features designed to facilitate its use. An example of such a sensor and its use and construction may be found in U.S. application Ser. No. 11/199,524 titled "Medical Sensor and Technique for Using the Same" and filed on Aug. 8, 2005, which is hereby incorporated by reference in its entirety for all purposes. As will be appreciated by those of ordinary skill in the art, however, such discussion is merely an example and is not intended to limit the scope of the present disclosure.

Figure 2:
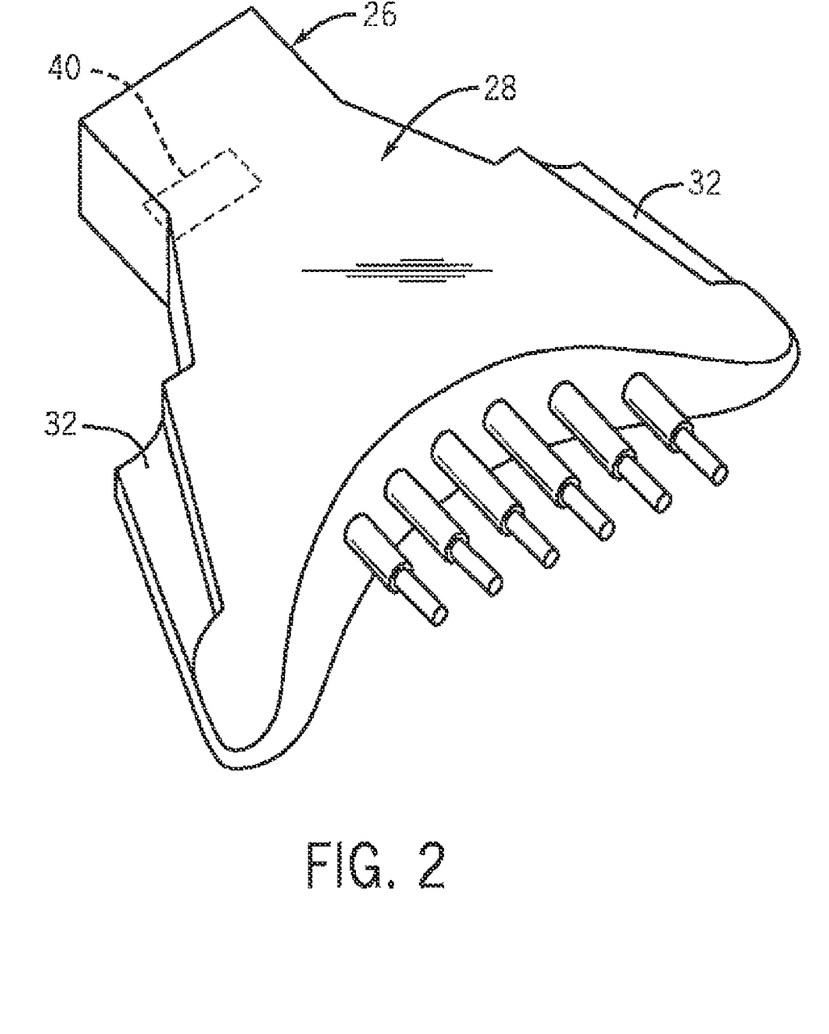
FIG. 2 illustrates a perspective view of a strain relief, in accordance with an embodiment.

Referring now to FIG. 2, a strain relief 26 of the sensor 10 is depicted in accordance with an embodiment. As depicted, the strain relief 26 may include a single body 28. Further, as depicted in FIG. 2, the strain relief 26 and the body 28 may include various features that facilitate assembly of the strain relief 26 to a sensor frame, such as a frame 30 discussed in further detail below with regard to FIGS. 3A-3B. For example, in one embodiment, the body 28 of the strain relief 26 includes extensions 32 that are located on each side of the body 28. As illustrated, the extensions 32 may include a wing-like structure extending along the length of the body 28 that can be inserted into a complementary frame slot 34 of the frame 30.

Figure 3A:
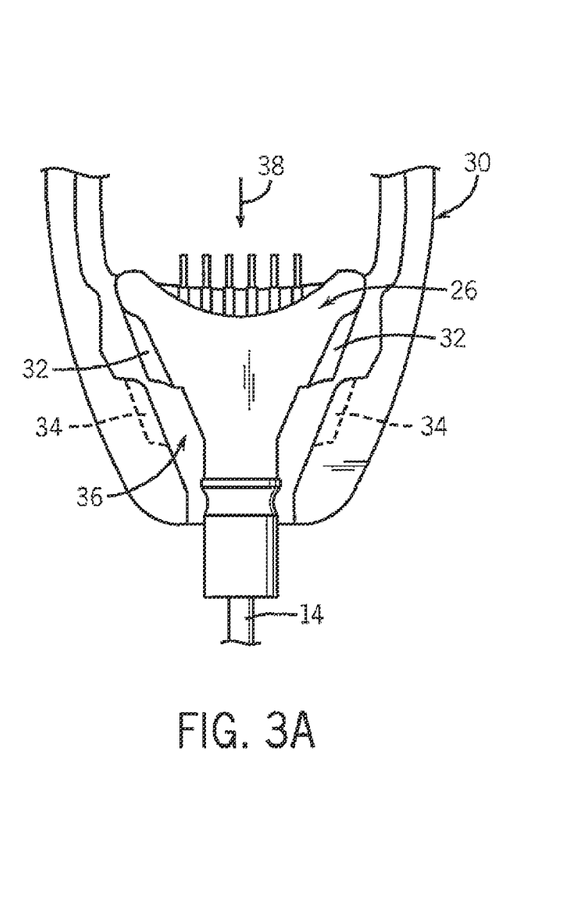
FIG. 3A illustrates a strain relief in a frame prior to engaging the frame, in accordance with an embodiment.
Figure 3B:
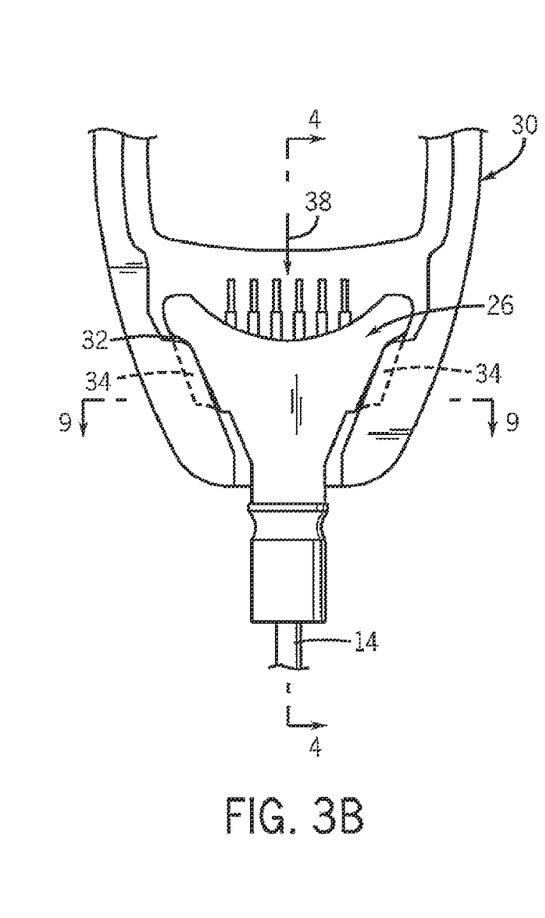
FIG. 3B illustrates a strain relief engaged in a frame, in accordance with an embodiment.

In an embodiments, as depicted in FIG. 3A, the strain relief 26 may be inserted into a void portion 36 of the frame 30, the extensions 32 aligned with the frame slots 34, and the strain relief 26 slid in an engagement direction (indicated by arrow 38) toward the frame slots 34 until the strain relief 26 is sufficiently seated in the frame 30, as depicted in FIG. 3B. Accordingly, integrating the extensions 32 into the strain relief 26 may facilitate rapid and secure assembly of the sensor 10. The number, location, size, shape and other characteristics of the extensions 32 and/or frame slot 34 may be varied to accommodate other embodiments without altering the implementation of the present disclosure.

Figure 4:
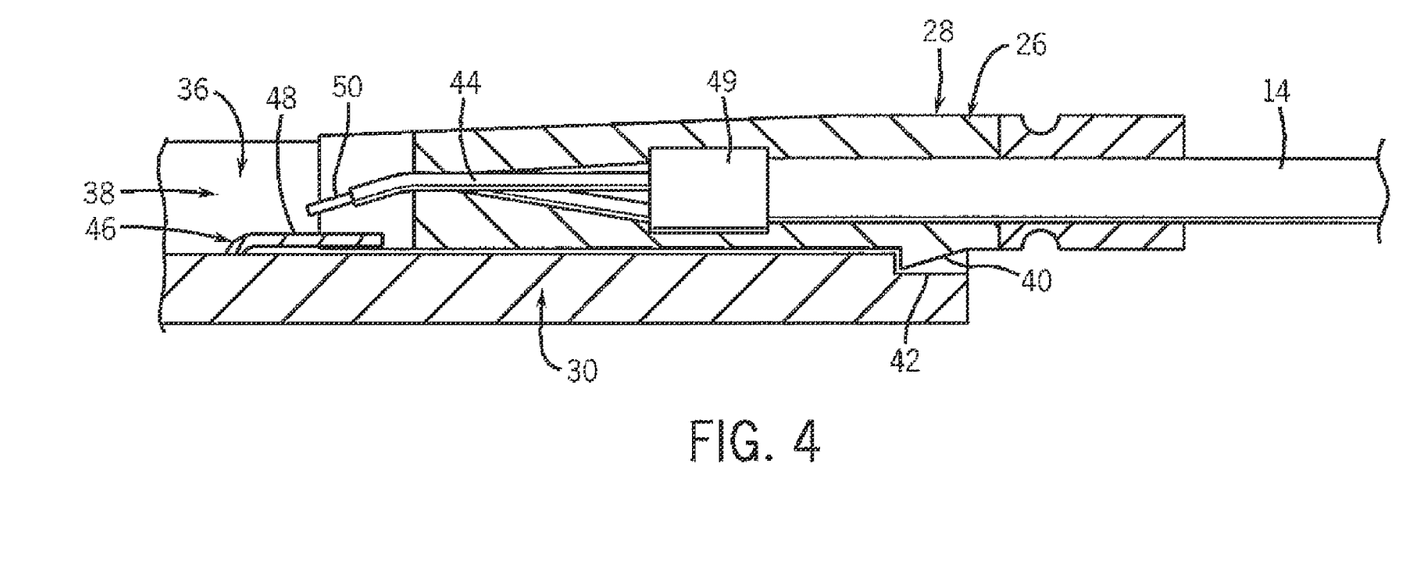
FIG. 4 illustrates a cross sectional view of the strain relief and frame of FIG. 3B, taken along line 4-4 of FIG. 3B.

Further, as depicted in FIG. 2 and further depicted in FIG. 4, embodiments of the strain relief 26 may also include a strain relief detent feature 40 that can be configured to mate with a complementary capture feature 42 of the frame 30. The engagement of the detent feature 40 with the complementary capture feature 42 may facilitate securing the strain relief 26 to the frame 30 when the extensions 32 and frame slot 34 are aligned, and the strain relief 26 is slid into position (see FIGS. 3A, 3B, and 4). For example, as depicted in FIG. 4, the strain relief detent feature 40 may include a raised lip or extension and the complementary capture feature 42 includes a recessed notch, channel, or the like. When the strain relief 26 is mated with the frame 30, the strain relief detent feature 40 may engage the complementary capture feature 42. The configuration, design, and number of the strain relief detent feature 40 and the strain relief capture feature 42 may be varied to facilitate retention of the strain relief 26 to the frame 30. For example, in other embodiments, the detent feature 40 may be disposed on the frame 30 and the complementary capture feature 42 may be disposed on the strain relief 32. Further, any number of detent features 40 and/or capture features 42 may be employed.

The engagement of the strain relief detent feature 40 to the strain relief capture feature 42 may be accompanied by an audible indication capable of being heard by an assembler. The audible indication may include a confirmatory click or snap upon engagement of the strain relief 26 and the frame 30. The audible indication may alert the assembler that the strain relief 26 and the frame 30 have been properly secured to one another. For example, the detent feature 40 and the capture feature 42 may engage one another to produce an audible snap or click within the last 10% of coupling the strain relief 26 to the frame 30 such that the audible snap is a signal to the assembler that the components have been sufficiently engaged.

Figure 5:
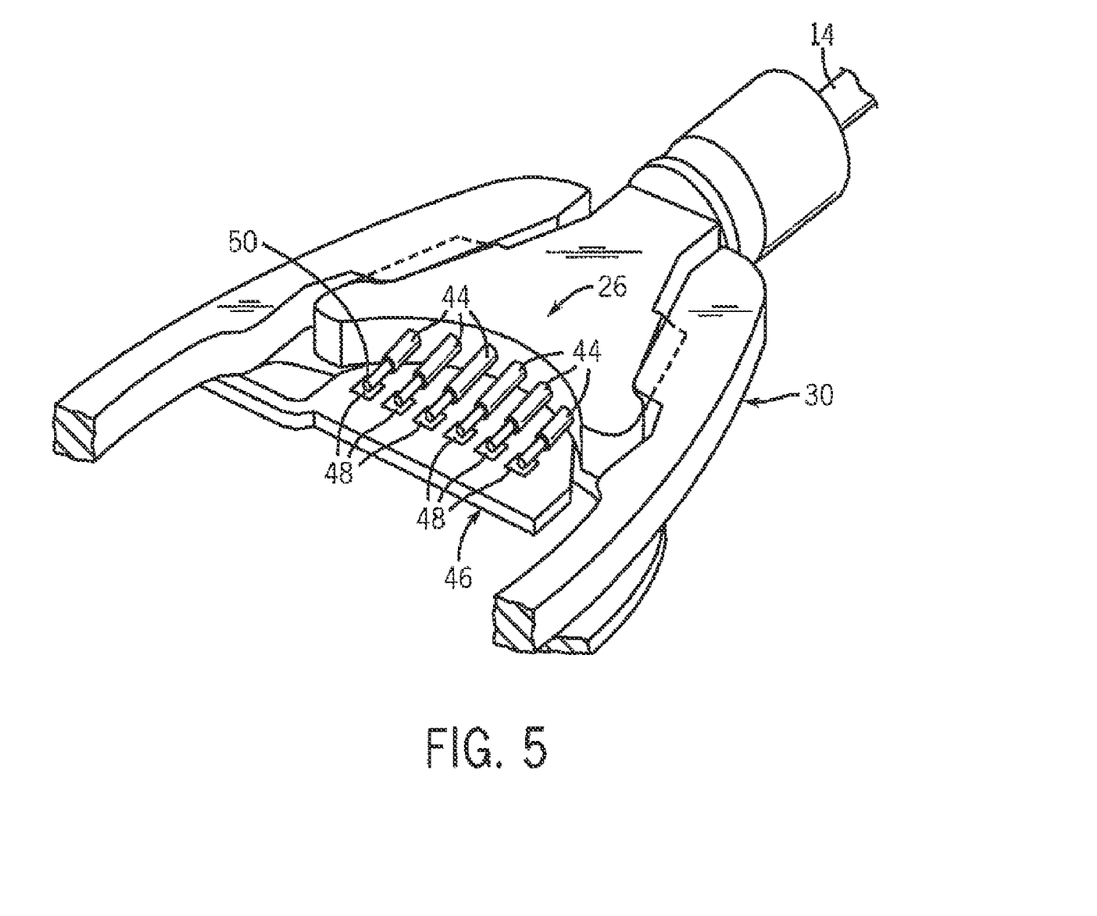
FIG. 5 illustrates a perspective view the strain relief, the frame, and the wire leads of FIGS. 3A and 3B aligned to the solder pads of the flex circuit, in accordance with an embodiment.

In addition to providing support for the cable 14, the strain relief 26 may also separate and align wire leads 44 of the cable 14, as illustrated in FIGS. 4 and 5. Separating and aligning the wire leads 44 may facilitate connection of the wire leads 44 to other devices, such as a flex circuit 46 including soldering pads 48. For example, where the cable 14 includes a crimp 49, the portion of the wire leads 44 between the crimp 49 and ends 50 of the wire leads 44 may be separated and coupled to respective electrical connectors, such as the soldering pads 48. By aligning the leads 44 at the time the strain relief 26 may be secured about the wire leads 44, the step of separating the wire leads 44 before securing the wire leads 44 to the flex circuit 46 may be simplified or eliminated, thereby, reducing the labor involved in assembling the sensor 10. Further, the separation and alignment of the wire leads 44 provided for by the strain relief 26 may stabilize the wire leads 44 during the assembly process, thus, further reducing the labor required to hold the wire leads 44 in place for connection (e.g., soldering). For example, as depicted in FIGS. 4 and 5, the strain relief 26 may be formed with the crimp 49 already installed about the cable 14 and six of the wire leads 44 properly positioned for soldering the ends 50 of the wire lead 44 to the soldering pads 48.

Figure 6:
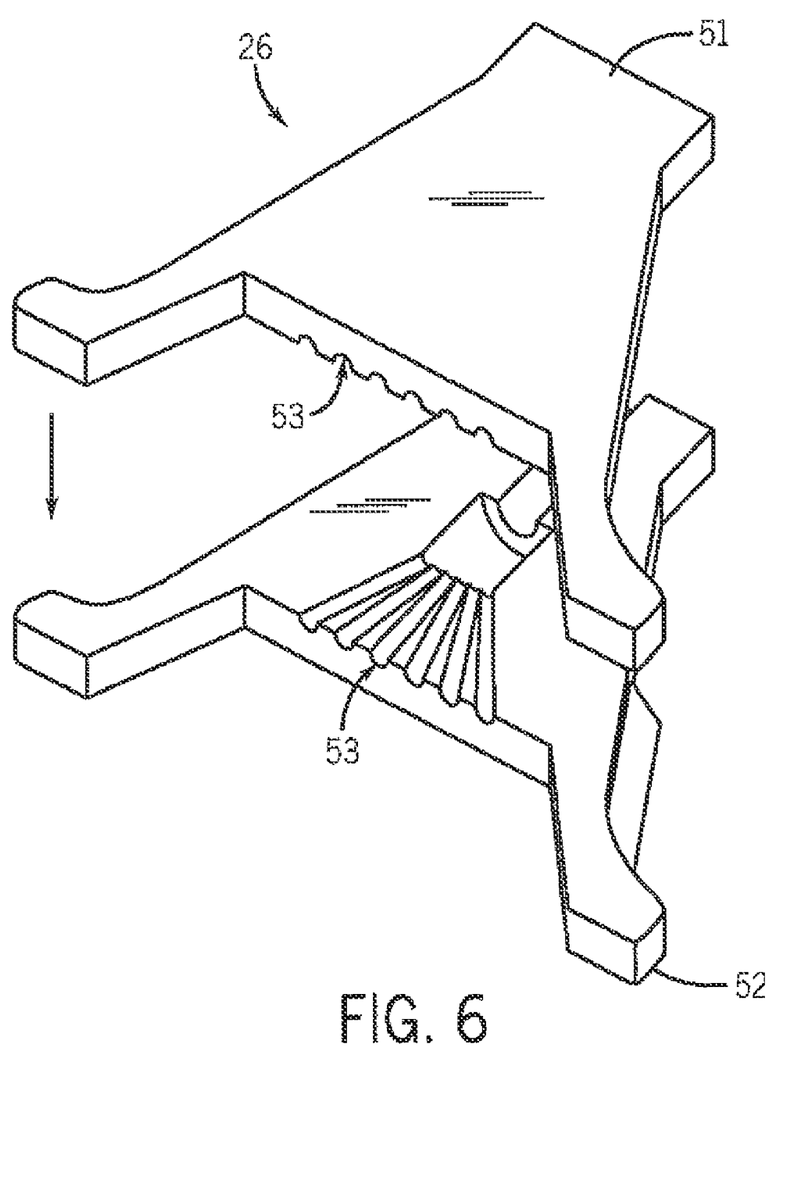
FIG. 6 illustrates an exploded view of the two portions of the strain, in accordance with an embodiment.

In another embodiment, the strain relief 26 may be formed from multiple portions that can be disposed about the wire leads 44. For example, as illustrated in FIG. 6, the strain relief 26 may include a top portion 51 and bottom portion 52. In the depicted embodiment, the top portion 51 and the bottom portion 52 each include a series of pass-through channels 53 that are configured to accept the wire leads 44. Each wire lead 44 may be set in a respective channel 53, and the top 51 and bottom 52 portions subsequently secured about the wire leads 44 and the crimp 49. For example, in an embodiment including the six wire leads 44, as discussed with regard to FIG. 5, the top portion 51 and the bottom portion 52 may each include six channels 53 that can each accept a respective wire lead 44. The number, arrangements, shape, and size of the channels 53 may be varied to accommodate various applications.

In various embodiments, the strain relief 26 may include two different regions, in another embodiment. For example, referring now to FIG. 7, in the illustrated embodiment, the strain relief 26 includes a first portion 54 and a second portion 56. The first portion 54 may include a structure that provides structural support and retention of the strain relief 26 in the frame 30. For example, in the depicted embodiment, the first portion 54 includes extensions 32 and the portion of the body 28 that may be disposed internal to the frame 30. The second portion 56 may extend about the cable 14 and, thus, may provide flexible support of cable 14 and reduce the likelihood of the cable 14 bending and wearing at the point of attachment to the first portion 54 and/or the frame 30.

Figure 7:
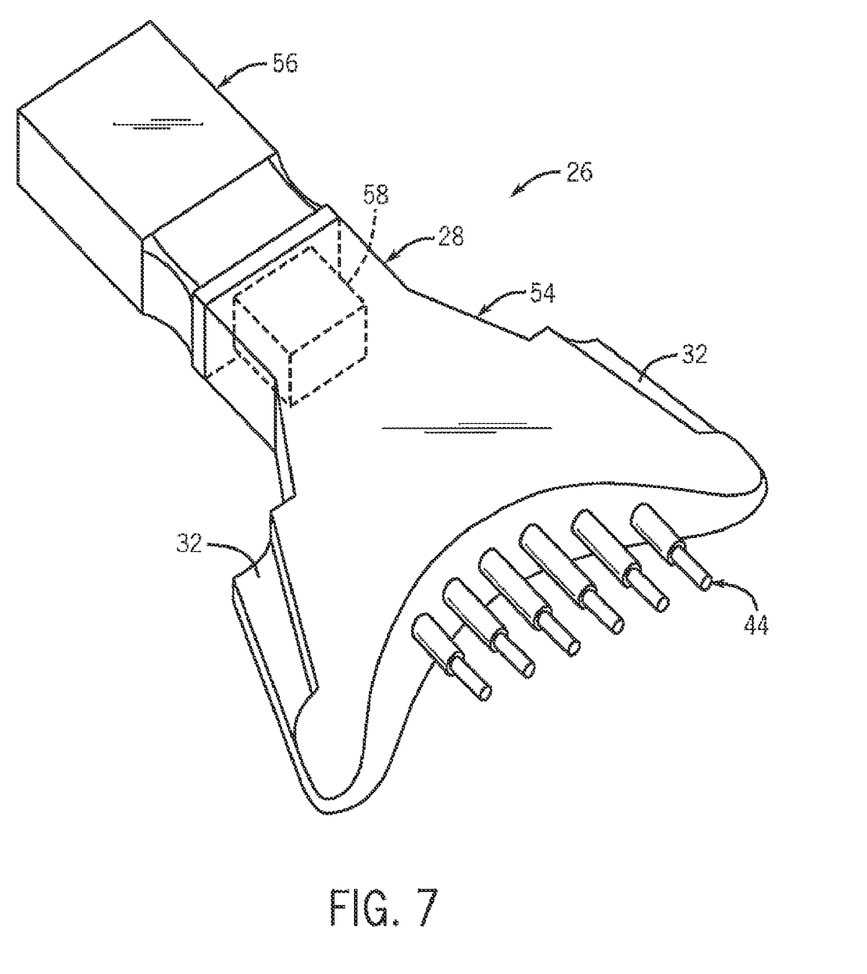
FIG. 7 illustrates a perspective view of a strain relief formed from two portions, in accordance with an embodiment.

In an embodiment, the first portion 54 and the second portion 56 may be formed from the same or different materials. In the case of different materials being employed for the first and second portions 54 and 56, the first portion 54 may employ a relatively hard material and the second portion 56 may be formed from a relatively soft material. For example, the first portion 54 may be formed from materials such as polypropylene and/or polystyrene, and the second portion 56 may be formed from a softer material, such as an ethylene propylene rubber. In other embodiments, the second portion 56 may be formed from materials having a durometer of about 45 Shore A to about 70 Shore A.

In various embodiments, the first portion 54 and the second portion 56 may be formed in a variety of manners. For example, in one embodiment, the strain relief 26 may include the first portion 54 and the second portion 56 formed integrally. In other words, the first portion 54 and the second portion 56 may be formed together such that they are mechanically coupled to one another to form the body 28. For example, as illustrated in FIG. 7, the first portion 54 may be formed to include a cavity 58, and the second portion 56 subsequently formed (e.g., molded) into the cavity 58, or vice versa, to form the strain relief 26.

Figure 8:
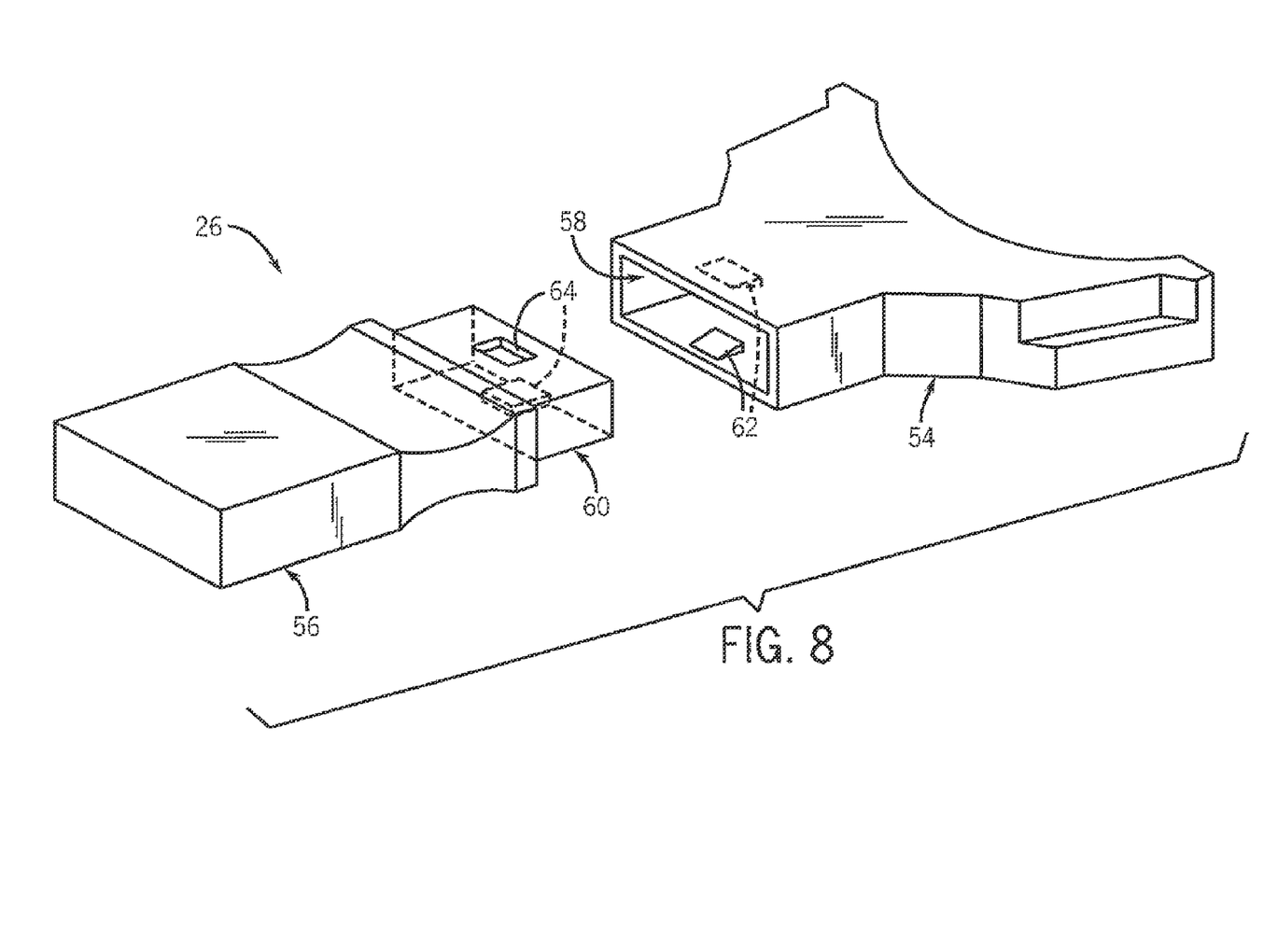
FIG. 8 illustrates an exploded view of the strain relief prior to assembly in accordance with an embodiment.

In another embodiment, the first portion 54 and the second portion 56 may be formed independently from one another and subsequently secured to one another to form the strain relief 26. For example, as depicted in FIG. 8, the cavity 58 of the first portion 54 may be configured to mate with a complementary protrusion 60 that extends from the second portion 56. During assembly, the protrusion 56 may be inserted into the cavity 58 to secure the first portion 54 and the second portion 56 to one another. For example, an interference fit between the protrusion 60 and the cavity 58 may provide enough friction to couple the first portion 54 and the second portion 56 to one another.

Another embodiment may employ detent features that are configured to facilitate coupling the first portion 54 and the second portion 56. For example, as further depicted in FIG. 8, the first portion 54 may include detent features 62 that are mated with complementary capture features 64 disposed on the surfaces of the second portion 56. For example, the detent feature 62 may include a raised surface, bump, or lip, and the capture feature 64 may include a depression, recess, notch, or lip that is configured to accept the detent feature 62. Accordingly, mating the detent feature 62 with the capture feature 64 may secure the first portion 54 to the second portion 56. The detent and capture features 62 and 64 may be arranged in a variety of manners. For instance, the capture feature 64 and/or the protrusion 60 may be integral to the first portion 54, and the detent feature 62 and/or the cavity 58 may be located integral to the second portion 56. Further, the number, location, size and combination of detent features 62 and capture features 64 may be varied. For example, a combination of detent and capture features 62 and 64 may be employed on, both, the first portion 54 and the second portion 56.

In various embodiments, the engagement of the detent feature 62 to the capture feature 64 may be accompanied by an audible indication capable of being heard by an assembler. The indication may be of the form of a confirmatory click or snap upon engagement of the first portion 54 and second portion 56. The audible indication may alert the assembler that the first portion 54 and the second portion 56 have been properly secured to one another. For example, the detent feature 62 and the capture feature 64 may engage one another and produce the audible indication within the last 10% of coupling the first portion 54 to the second portion 56 such that the audible indication is a signal to the assembler that the components have been sufficiently assembled.

Figure 9:
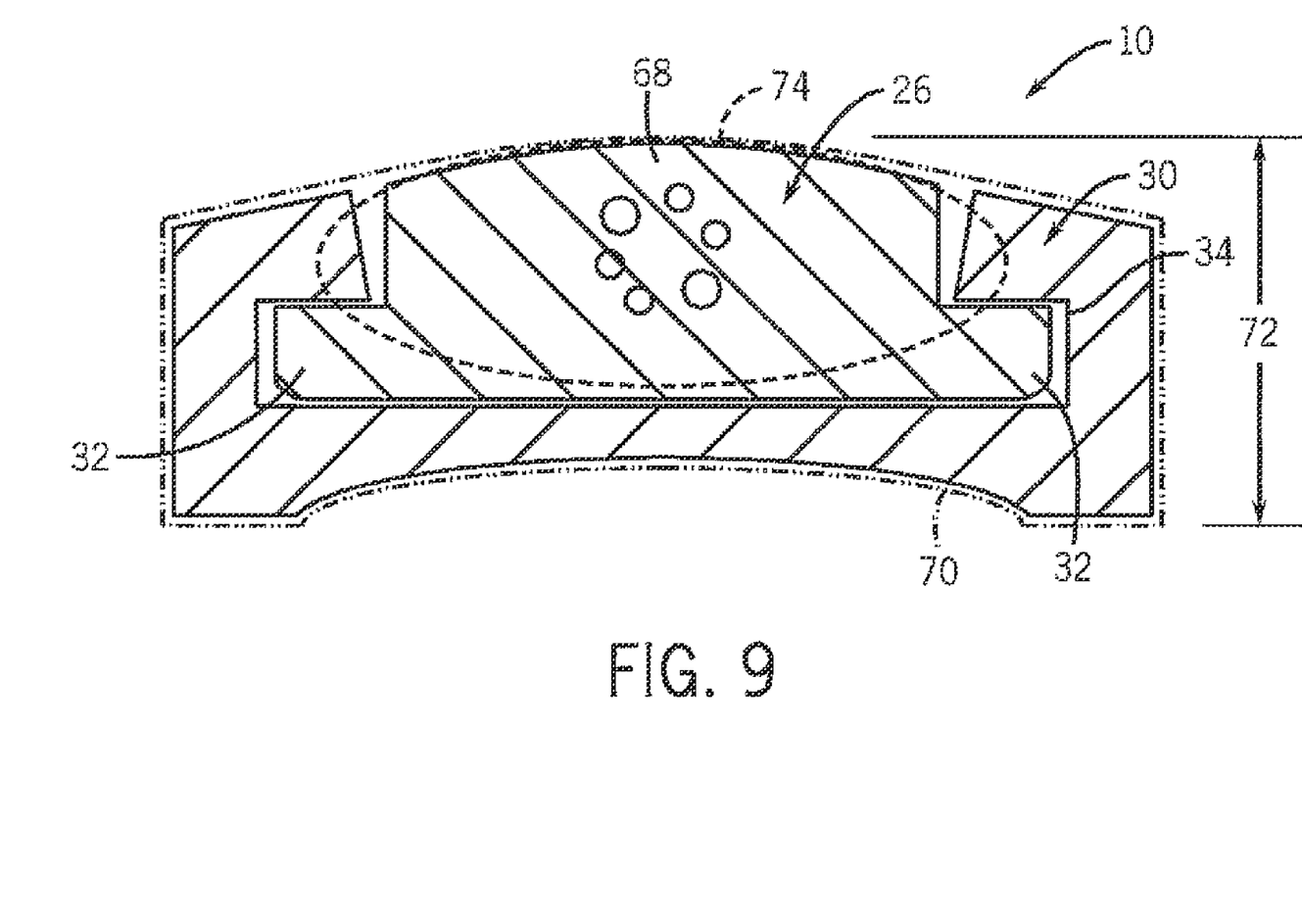
FIG. 9 illustrates a cross sectional view of the strain relief and frame of FIG. 3B, taken along line 9-9 of FIG. 3B, in accordance with an embodiment.

Turning now to FIG. 9, an embodiment of the strain relief 26 may include a surface feature 68 that substantially conforms to the shape and/or curvature of the assembled sensor 10, including an overmold. For example, in the illustrated embodiment, the surface feature 68 (e.g., the top surface) of the strain relief 26 includes a curvature that is substantially the same as the curvature of an overmold 70 that is disposed about the sensor 10 during a fabricating process. In such an embodiment, the surface feature 68 may be shaped or contoured to provide the desired shape or curvature of the sensor 10 when overmolded. For example, as depicted in FIG. 9, the surface feature 68 may include a dome that is substantially consistent with the curvature of the top of the sensor frame 30. By conforming the surface feature 68 to the shape of the overmold 70, an additional shaping component does not need to be added between the strain relief 26 and the overmold 70. Further, the absence of such a shaping component may allow an overall height 72 of the sensor 10 to be reduced. As will be appreciated by those of ordinary skill in the art, the shape of the surface feature 68 may be varied to accommodate the resulting shape of the overmold 70, taking into account the consistency of the thickness of the overmold 70 over the surface feature 68.

In another embodiment, the strain relief 26 may occupy a majority of a void region 74 in the frame 30. For example, as depicted in FIG. 9, the strain relief 26 may occupy a majority of the internal void region 74 of the frame 30, thereby preventing air from otherwise filling the void region 74. Displacing some or all of the air that may otherwise remain in the frame 30 may prevent or reduce the formation of air bubbles during an overmolding process.

In various embodiments, materials suitable for forming the strain relief 26 may include thermoplastic elastomers (TPE) that may facilitate chemically bonding to an overmold material 70, and may provide sufficient rigidity to support the retention of the cable 14 in the frame 30. For example in one embodiment, the strain relief 26 may be formed from polypropylene which is generally capable of chemically bonding to overmold materials, including GLS 2706 and GLS G6713, available from GLS Corporation headquartered in McHenry, Ill., USA.

In another embodiment, the material used to form the strain relief 26 may include a transparent material. For example, in one embodiment the strain relief 26 may be formed of a transparent polypropylene material. A transparent material may provide for visual inspection of the strain relief 26, and may facilitate alignment, assembly, and/or final testing of the sensor 10. For example forming the strain relief 26 of transparent material may facilitate inspection of the condition and placement of the wire leads 44 and the wire crimp 49 prior to assembly and or overmolding of the sensor 10. As will be appreciated by those of ordinary skill in the art, other materials may be employed that provide sufficient support and transparency (e.g., transparent polystyrene).

Figure 10:
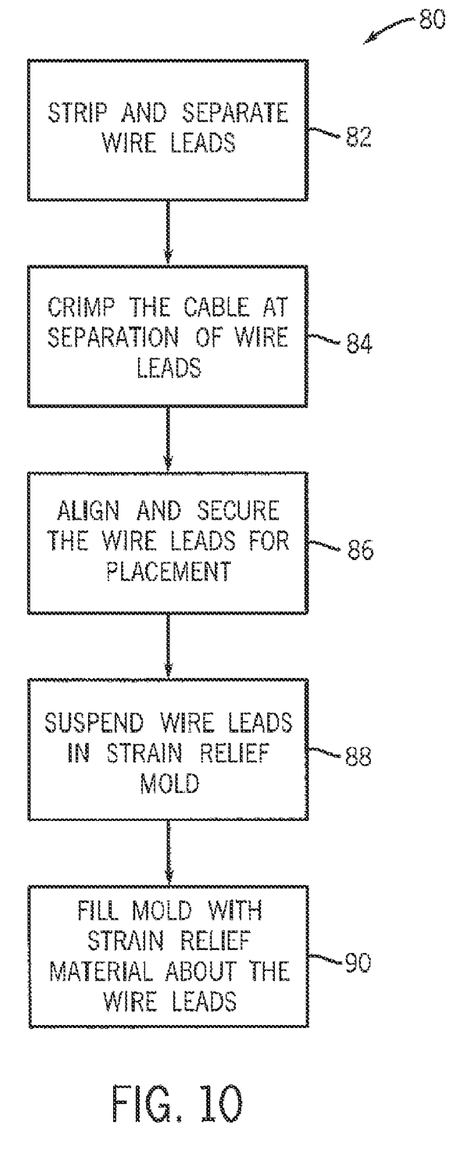
FIG. 10 is a flowchart that illustrates a method for forming the strain relief, in accordance with an embodiment.

FIG. 10 is a flowchart that illustrates a method 80 of manufacturing the strain relief 26 about the wire leads 44, according to an embodiment. First, the cable 14 may be stripped of insulation and the individual wire leads 44 stripped and separated (Block 82). The crimp 49 may then be placed about the end of the cable 14 (Block 84) to prevent separation of the cable 14 proximate the location where the wire leads 44 are separated. The wire leads 44 may then be spread, aligned, and secured (Block 86) for coupling to the flex circuit 46. After the wire leads 44 are secured into relative placements, the wire leads 44 may be suspended in a mold used to form the strain relief 26 (Block 88). With the wire leads 44 suspended in the mold, the strain relief 26 material (e.g., polypropylene) may be injected about the suspended wire leads 44 to fill the mold and form the strain relief 26 (Block 90).

In various embodiments, the method 80 may provide for a solid strain relief 26 molded about the aligned wire leads 44. As will be appreciated by a person of ordinary skill in the art, the method 80 of forming the strain relief 36 about the aligned wire leads 44 may include other methods to secure the strain relief 26 about the aligned wire leads 44. For example, as depicted in FIG. 6, the strain relief 26 may include top and bottom portions 51 and 52 that include multiple pass-through channels 53 that are configured to accept the wire leads 44 and the crimp 49. The wire leads 44 may set in the pass-through channels 53 and the top and bottom portions 51 and 52 may then be secured about the wire leads 44 and crimp 49 to form the strain relief 26 about the aligned wire leads 44.

Figure 11:
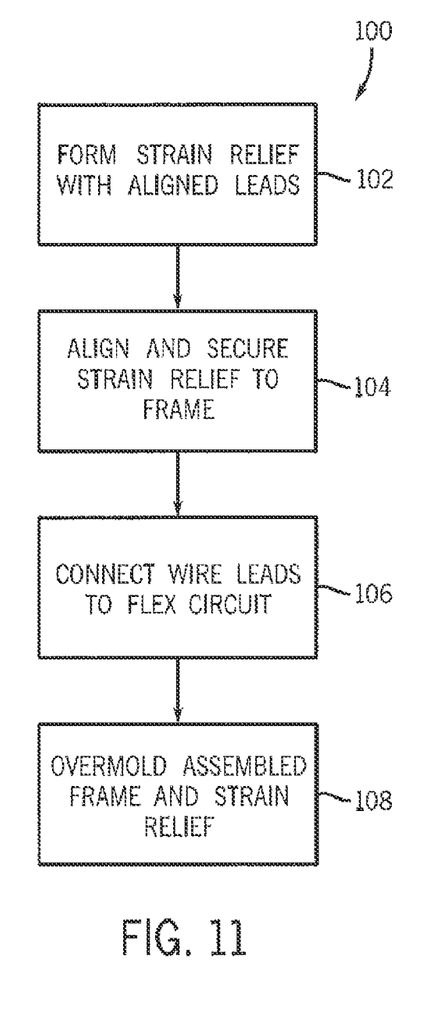
FIG. 11 is a flowchart that illustrates of a method for manufacturing a sensor with a strain relief, in accordance with an embodiment.

FIG. 11 is a flowchart that illustrates a method 100 of manufacturing a sensor 10 in accordance with an embodiment. The method 100 provides for manufacturing of the strain relief 26, assembly of the strain relief 26 to the sensor frame 30, and overmolding of the assembled sensor 10. For example, the embodiment of FIG. 11 provides for forming strain relief 26 with aligned wire leads 44 (Block 102) as described herein.

In various embodiments, the method 100 may also include aligning and securing the strain relief 26 to the frame 30 (Block 102). Securing the strain relief 26 to the frame 30 may provide for mechanically aligning and fastening the strain relief 26 and holding the strain relief 26 in place during subsequent assembly and use. For example, as described previously, securing the strain relief 26 to the frame 30 may require alignment of the extensions 32, sliding the strain relief 26 into the frame 30, and continuing to slide the strain relief 26 until the strain relief detent feature 40 engages the complementary capture feature 42. As described previously, the engagement of the strain relief detent feature 40 and the capture feature 42 may be indicated audibly.

To facilitate connection of the wire leads 44 to flex circuit 46, the method 100 may also include connecting the wire leads 44 of the cable 14 to the flex circuit 46 (Block 106). As will be appreciated by a person of ordinary skill in the art, connecting the wire leads 44 to the flex circuit 46 may include various means of electrical coupling, including soldering the ends 50 of the wire leads 44 to the solder pads 48.

In various embodiments, the method 100 may also include overmolding the assembled frame 30 and strain relief 26 (Block 108). For example, after the strain relief 26 has been secured to the frame 30, it may be desirable to overcoat the sensor 10 with an overmold material to provide protection of the assembly (Block 108). As discussed previously, overmold materials may include GLS 2706 and GLS G6713 or any other suitable overmold material. During the overmold process, the curvature of the shape of the strain relief 26 may fill a majority of the void region 74 in the frame 30 and thereby reduce the amount of overmold material required to provide the desired shape of the sensor 10, as well as, reduce the propensity of the overmold 70 to form air pockets. The overmold 70 may provide additional protection to the sensor 10 and secure the strain relief 26, in addition to providing an ergonomic package for the user of the sensor 10.

While the medical sensors 10 discussed herein are some examples of overmolded or coated medical devices, other such devices are also contemplated and fall within the scope of the present disclosure. For example, other medical sensors and/or contacts applied externally to a patient may be advantageously applied using the strain relief 26 having alignment and retaining features, as discussed herein. For example, devices for measuring tissue water fraction or other body fluid related metrics may utilize a sensor as described herein. Likewise, other spectrophotometric applications where a probe is attached to a patient may utilize a sensor as described herein.

While the disclosure may be susceptible to various modifications and alternative forms, specific embodiments have been shown by way of example in the drawings and have been described in detail herein. However, it should be understood that the disclosure is not intended to be limited to the particular forms disclosed. Rather, the disclosure is to cover all modifications, equivalents, and alternatives falling within the spirit and scope of the disclosure as defined by the following appended claims.

What is claimed is:

1. A sensor assembly, comprising:
   a pulse oximetry sensor coupled to a frame, the pulse oximetry sensor comprising at least one emitter and detector;
   a cable coupled to the emitter and detector;
   a strain relief body capable of providing support for connection of the cable to the emitter and the detector; and
   an alignment feature capable of facilitating alignment of the strain relief body relative to the frame.

2. The sensor assembly of claim 1, wherein the strain relief body comprises polypropylene.

3. The sensor assembly of claim 1, wherein the strain relief body comprises a generally transparent material.

4. The sensor assembly of claim 1, wherein the strain relief body comprises a first portion and a second portion, wherein the first portion is capable of facilitating support and/or retention of the strain relief body in the frame, and the second portion is capable of facilitating support of the cable.

5. The sensor assembly of claim 4, wherein the second portion comprises a material generally having a durometer rating of about 45 A to about 70 A.

6. The sensor assembly of claim 4, wherein the two portions are coupled to one another via a locking feature.

7. The sensor assembly of claim 6, wherein the locking feature facilitates an audible indication when the two portions are coupled.

8. The sensor assembly of claim 1, wherein the alignment feature comprises an extension configured to align with a complementary slot on the frame, wherein sliding the extension into the complementary slot secures the strain relief body to the frame.

9. The sensor assembly of claim 1, wherein the strain relief body comprises a retention feature configured to engage a complementary retention feature on the frame.

10. The sensor assembly of claim 9, wherein the retention feature is configured to provide an audible indication when the retention feature engages the complementary retention feature.

11. The sensor assembly of claim 1, wherein the strain relief body is molded generally about the cable and/or wire leads coupled to the cable.

12. The sensor assembly of claim 1, wherein the strain relief body comprises two portions configured to facilitate alignment and support of the cable and wire leads coupled to the cable, wherein one portion comprises an accepting channel configured to secure the cable and/or the wire lead, and wherein the two portions are secured to one another about the cable and/or the wire leads.

13. The sensor assembly of claim 1, wherein the strain relief body comprises a surface feature that generally conforms to the shape and/or curvature of the frame.

14. A sensor assembly, comprising:
   a cable comprising wire leads;
   a strain relief body coupled to the cable at a first end of the strain relief body and capable of separating the wire leads within the strain relief body, wherein the wire leads exit the strain relief body from a second end in a separated configuration;
   a flexible circuit coupled to the wire leads in the separated configuration; and
   at least one emitter and detector, wherein the emitter and the detector are coupled to the flexible circuit.

15. The sensor assembly of claim 14, wherein the flexible circuit comprises a plurality of soldering pads and wherein the wire leads are separated to align with at least a portion of the plurality of soldering pads.

16. The sensor assembly of claim 14, wherein the strain relief body comprises a plurality of channels configured to receive at least one wire lead.

17. The sensor assembly of claim 16, wherein the plurality of channels form a fan shape within the strain relief body, wherein a widest portion of the fan shape is proximate to the second end.

18. The sensor assembly of claim 14, wherein the emitter and the detector are disposed on the flexible circuit.

19. A sensor assembly, comprising:
   a frame;
   a photometric sensor coupled to the frame;
   a cable encompassing one or more wire leads; and
   a strain relief body comprising:
      a first end coupled to the cable;
      a second end coupled to the photometric sensor via the one or more wire leads, wherein the wire leads exit the cable within the strain relief body; and
      alignment members extending from the strain relief body between the first end and the second end, wherein the alignment members are configured to couple the strain relief body to the frame.

20. The sensor assembly of claim 19, wherein the alignment members are configured to slide into receiving members on the frame.

* * * * *